(12) United States Patent
Sandberg

(10) Patent No.: US 6,770,679 B1
(45) Date of Patent: Aug. 3, 2004

(54) COMPOUNDS FROM EPOXIDISED NITRILES, PROCESS FOR THEIR PRODUCTION AND USE AS CLEANING AGENTS

(75) Inventor: Elina Sandberg, Odsmal (SE)

(73) Assignee: Akzo Nobel N.V, Arnhem (NL)

( * ) Notice: Subject to any disclaimer, the term of this patent is extended or adjusted under 35 U.S.C. 154(b) by 22 days.

(21) Appl. No.: 10/018,871
(22) PCT Filed: Jun. 19, 2000
(86) PCT No.: PCT/SE00/01285
§ 371 (c)(1),
(2), (4) Date: Mar. 4, 2002
(87) PCT Pub. No.: WO01/00567
PCT Pub. Date: Jan. 4, 2001

(30) Foreign Application Priority Data

Jun. 29, 1999 (SE) .............................. 9902450

(51) Int. Cl.$^7$ ....................... B01F 17/42; C97C 255/13; C97C 235/06; C97C 253/30; C11D 1/72
(52) U.S. Cl. ....................... 516/203; 558/358; 558/447; 558/451; 564/131; 564/201; 510/194; 510/219; 510/220; 510/324; 510/499; 510/502
(58) Field of Search .......................... 516/203; 558/258, 558/447, 451; 564/131, 201; 510/194, 219, 220, 324, 499, 502

(56) References Cited

U.S. PATENT DOCUMENTS

| | | | | |
|---|---|---|---|---|
| 3,119,848 A | * | 1/1964 | Wrigley et al. ................ | 516/67 |
| 3,281,438 A | * | 10/1966 | Johnson ........................ | 516/203 |
| 4,356,128 A | * | 10/1982 | Rogier ......................... | 558/451 |
| 4,678,562 A | * | 7/1987 | Keys ............................ | 252/61 |
| 6,004,923 A | * | 12/1999 | Oftring et al. ............... | 510/499 |

FOREIGN PATENT DOCUMENTS

| | | | |
|---|---|---|---|
| CA | 2146236 | 4/1994 | ......... C07C/69/708 |
| EP | 0 374 922 A2 | 6/1990 | ......... C07C/69/708 |
| EP | 0 754 667 A2 | 1/1997 | ........... C07C/43/15 |
| GB | 2 055 821 A | 3/1981 | ......... C07D/301/12 |
| WO | WO 94/07840 | 4/1994 | ......... C07C/69/708 |
| WO | WO 01/00605 A1 | * 1/2001 | |

OTHER PUBLICATIONS

Derwent Abstract No.: 011111308 abstracting European Patent No. 0 754 667 A2, week 199709.
International Search Report dated: Oct. 11, 2000: PCT/SE 00/01285.
Analytical Chemistry vol. 36 No. 3 pp. 667–668; Direct Titration of Epoxy Compounds and Aziridines, Mar. 1964.
The Journal of the American Oil Chemists' Society vol. 39 pp. 80–84; The Oxyethylation of 9, 10–Octadecanediols and 9, 10–Dihydroxystearonitrile. Nonionic Soaps, $^1$Feb. 1962.
Organic Syntheses Coll. vol. II pp. 586–587, date unknown.

* cited by examiner

Primary Examiner—Daniel S. Metzmaier
(74) Attorney, Agent, or Firm—Ralph J. Mancini; Michelle J. Burks

(57) ABSTRACT

The present invention relates to nonionic compounds of the polyoxymethylene type that are low-foaming and can be used as surfactants, especially in cleaning compositions at an alkaline pH. They are obtained from unsaturated nitriles, that have been epoxidised with e.g. hydrogen perroxide, and alkyl blocked polyalkylene glycols. The nonionic nitrile surfactants can be reacted further with e.g. hydrogen peroxide under alkaline conditions to obtain nonionic amide surfactants. Amide derivatives of this type could also be obtained by reaction between ammonia or a primary or secondary amine and an acid or ester. The nonionic compounds exhibit one or several structure elements according to formula (II)

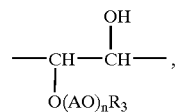

in the aliphatic carbon chain where AO is an alkyleneoxy group containing 2–4 carbon atom, R3 is an alkyl group with 1–4 carbon atoms and n is a number between 1 and 30.

17 Claims, No Drawings

COMPOUNDS FROM EPOXIDISED NITRILES, PROCESS FOR THEIR PRODUCTION AND USE AS CLEANING AGENTS

The present application was filed on Jun. 19, 2000 as international application serial number PCT/SE00/01285 and claims priority of Swedish patent application No. 99002450-7 filed on Jun. 29, 1999.

The present invention relates to nonionic compounds of the polyoxyalkylene type that are low-foaming and can be used as surfactants, especially in cleaning compositions at an alkaline pH. They are obtainable from unsaturated nitriles, that have been epoxidised with e.g. hydrogen peroxide, and alkyl blocked polyalkylene glycols. The nitrile surfactants can be reacted further with e.g. hydrogen peroxide under alkaline conditions to obtain amides. Amide derivatives of this type can also be obtained from unsaturated acids or esters that have been epoxidised and thereafter reacted with alkyl blocked polyalkylene glycols. These acid or ester derivatives are transformed to the corresponding amide derivatives by reaction with ammonia or a primary or secondary amine.

Nonionic surfactants constitute an important group of surface-active compounds that are widely used in numerous applications. However, many of the ethylene oxide adducts containing a hydrophobic chain with 12–22 carbon atoms are too high-foaming to be used in certain applications, such as e.g. machine dish-washing, machine washing of textiles, bottle cleaning and cleaning of hard surfaces.

It has been suggested in EP-A2-0 754 667 to produce new nonionic surfactants, that would generate less foam, by reacting an epoxidised fatty acid ester with a polyglycol ether. These ring-opened products are claimed to be particularly suited to be used as defoamers in a variety of applications. In WO 94/07840 similar products are obtained by reacting epoxidised esters with fatty alcohol polyglycol ethers. These products are claimed to be low-foaming and to have a good biodegradability, and are used as auxiliaries in the removal of water from solid materials.

However, there is a drawback when using the ester polyglycol ether compounds, since the ester group is readily hydrolysed when subjected to highly alkaline conditions. This excludes applications where a high pH is required, since the nonionic product would then be converted to an anionic product.

Nonionic products containing a cyano group, which is a more stable functional group than the ester group, have been described by Wrigley, Smith and Stirton (J. Am. Oil Chem. Soc. 39:80–84 (1962)). These surfactants were obtained by treatment of an unsaturated nitrile with 98% formic acid and 30% hydrogen peroxide to give the hydroxy-formate, followed by mild hydrolysis to yield the dihydroxy compound, which was then ethoxylated using KOH as a catalyst. However, since both the hydroxyl groups of the intermediate product are secondary, the final product will not be very-well defined. Once an ethylene oxide unit has been attached to the secondary hydroxyl group, there will be a primary hydroxyl group present, which will add another ethylene oxide unit much faster than the remaining secondary groups. The end result will be a product where one of the polyoxyethylene chains is much longer than the other, a lot of the polyoxyethylene homologues will probably contain only short chains, and some part of the hydrophobic diol will even be unreacted. Thus, in the above-mentioned article it is stated that ethoxylation of 9,10-dihydroxystearonitrile with 4 moles of ethylene oxide leaves 5.9% of starting diol.

Consequently there is a need for low-foaming products that are more stable than the prior known ester polyglycol ethers and better defined than the ethoxylated diol nitriles. The purpose of the present invention is to provide such products.

It has now been found that these objectives can be met by a new class of low-foaming well-defined compounds, which can easily be prepared from starting materials that are easy to handle and that can be obtained by standard procedures, by reacting an epoxidised nitrile with an alkyl blocked polyalkylene glycol. Since the compounds that are obtained are low-foaming, they are suitable to use e.g. in cleaning compositions for applications where low foam is required, such as vehicle cleaning, bottle cleaning and machine-washing. To obtain products with even better toxicological and environmental profiles that still are relatively stable, the nitrile group can be converted to an amide group by treatment with e.g. alkaline hydrogen peroxide. An amide derivative according to the invention could also be produced by the reaction between an acid or ester derivative of the type described in EP-A2-0 754 667 and ammonia or a primary or secondary amine.

The nonionic compounds according to the present invention are characterised by the general formula RY (I), where R is a substituted aliphatic group containing 1–3 structure elements with the formula

(II)

where the carbon atoms shown in the structure element are part of the aliphatic carbon skeleton of group R, which. contains 8–24 carbon atoms, preferably 12–22 carbon atoms, and Y is a nitrile or an amide group; $R_3$ is an alkyl group with 1–4 carbon atoms; AO is an alkyleneoxy group containing 2–4 carbon atoms and n is a number between 1 and 30, preferably 3–20. The number of structure elements contained in the chain is preferably 1–2.

Suitable examples of the above-mentioned compounds are those having the formulae

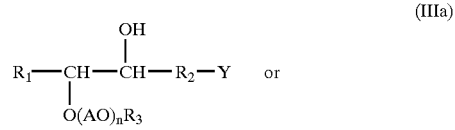
(IIIa)

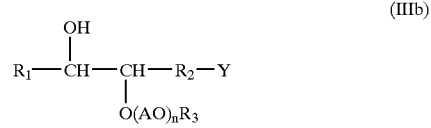
(IIIb)

where $R_1$ is an aliphatic group, $R_2$ is an aliphatic radical, the sum of carbon atoms contained in $R_1$ and $R_2$ is between 9 and 19 and $R_3$, AO, n and Y have the same meaning as above.

Suitable amide groups are those having the formula

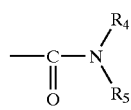

where $R_4$ and $R_5$ independently are H, an alkyl group with 1–6 carbon atoms, preferably 1–4 carbon atoms, or $(AO)_m$ where AO is an alkyleneoxy group containing 2–3 carbon atoms, preferably 2, and m is 1–20, preferably 1–2. Most preferably at least one of $R_4$ and $R_5$ is H.

The nonionic compounds according to the invention may be produced by
a) reacting an epoxidised nitrile containing 1–3 epoxy groups and a total of 8 to 24 carbon atoms, preferably 12–22 carbon atoms, with an alkyl blocked polyalkylene glycol having the formula $R_3O(AO)_nH$, where $R_3$, AO and n has the same meaning as in formula II, in the presence of a catalyst, and optionally subjecting the product obtained to alkaline hydrogen peroxide or
b) reacting ammonia or a primary or secondary amine with an acid or an ester containing 1–3 structure elements according to formula II in the aliphatic skeleton. The alkyleneoxy groups could be distributed randomly or in blocks or a mixture thereof. Normally at least 50% of the alkyleneoxy groups are ethyleneoxy groups. Alkyl blocked polyethylene glycols are the reactants most often used. Suitable examples of alkyl blocked polyalkylene glycols are $CH_3(CH_2CH(CH_3)O)_2(CH_2CH_2O)_{10}R$ and $CH_3(CH_2CH_2O)_{14}H$.

When the reaction between a monoepoxidised nitrile and the alkyl blocked polyalkylene glycol takes place, there is an equal chance for attack by the glycol on either of the two carbons in the epoxy ring. Consequently two regioisomers are formed in about the same amount, as is shown by formula IIIa and IIIb.

The epoxidised nitriles could be derived from unsaturated nitriles e.g. by using the Venturello method described in GB-A-2055821, where hydrogen peroxide is used as the source of active oxygen, or by the use of peracids. The unsaturated nitriles could contain more than one double bond, and the epoxidation of such polyunsaturated nitriles can consequently give rise to products containing more than one epoxy group. Accordingly, the nonionic compounds derived from such polyepoxidised nitrites could contain several polyoxyethylene chains distributed along the aliphatic skeleton. Naturally occurring fatty acids, which are the starting material for the nitrites, are normally mixtures between acids with different amounts of double bonds, and consequently the resulting end products will also be mixtures of compounds containing different numbers of polyoxyethylene chains.

The unsaturated nitriles are intermediates in the process for the manufacturing of fatty amines, and they are thus readily available in large quantities. Oleonitrile is a suitable example of an unsaturated nitrile, but also other nitrites derived from unsaturated acids would be possible to use. Examples of such acids are tall oil acid, linoleic acid, erucic acid and fish-oil acids, as well as unsaturated synthetic acids.

The reaction between the epoxynitriles and the alkyl blocked polyalkylene glycols could be catalysed both by acids, such as Lewis acids e.g. $BF_3$, and by alkali, such as alkoxides.

The conversion of the nitrile group to an amide group by the treatment with alkaline peroxide is described e.g. in Organic Synthesis Collective Vol. II p. 586.

The nonionic amide compounds according to the invention could also be obtained by a standard procedure via the suitable acid or ester derivatives by reaction with ammonia or an amine. Suitable examples of amines are primary or secondary alkylamines, ethanolamine and diethanolamine.

The following examples are illustrative of the invention and are not to be construed as limiting thereof.

EXAMPLE A

The product mixture according to formula IIIa and IIIb where $R_1=C_8H_{17}$, $R_2=C_7H_{14}$, AO=—$CH_2CH_2O$—, n=10, $R_3=CH_3$ and Y=—CN was prepared according to the following procedure:

0.01 mole boron trifluoride diethyl ether complex was added to 0.1 mole polyethylene glycol monomethyl ether (molecular weight=472.5) while stirring. The mixture was heated to 60° C., and with continued stirring 0.1 mole 9,10-epoxyoleonitrile was added during a period of 30 minutes. The reaction was exothermic, and the temperature was kept between 60–65° C. during the addition by alternately cooling and heating the reaction mixture. When all epoxide had been added, a sample was removed to determine the amount of unreacted epoxide present in the product. The method used for this analysis was a titration procedure, which is described in Analytical Chemistry 36 (1964) p667. The amount of epoxide was <1%. The product was also investigated by $^1$H-NMR, and the spectrum obtained was in accordance with the desired is structure.

Sodium bicarbonate was added to the product in order to remove $BF_3$. The slurry obtained was stirred for 15 minutes, and then filtered through a layer of sodium bicarbonate.

EXAMPLE B

The product mixture according to formula IIIa and IIIb where $R_1=C_8H_{17}$, $R_2=C_7H_{14}$, AO=—$CH_2CH_2O$—, n=14, $R_3=CH_3$ and Y=—CN was prepared according to the procedure described in Example A, except that the glycol used was polyethylene glycol monomethyl ether with a molecular weight of 649. The amount of unreacted epoxide in the product mixture was <1%, and the $^1$H-NMR spectrum was in accordance with the desired structure.

EXAMPLE C

The product mixture according to formula IIIa and IIIb where $R_1=C_8H_{17}$, $R_2=C_7H_{14}$, AO=—$CH_2CH_2O$—, n=7.2, $R_3=CH_3$ and Y=—CN was prepared according to the procedure described in Example A, except that the glycol used was polyethylene glycol monomethyl ether with a molecular weight of 350. The amount of unreacted epoxide in the product mixture was <1%, and the $^1$H-NMR spectrum was in accordance with the desired structure.

EXAMPLE D

The product mixture according to formula IIIa and IIIb where $R_1=C_8H_{17}$, $R_2=C_7H_{14}$, AO=—$CH_2CH_2O$—, n=11.8, $R_3=CH_3$ and Y=—CN was prepared according to the procedure described in Example A, except that the glycol used was polyethylene glycol monomethyl ether with a molecular weight of 550. The amount of unreacted epoxide in the product mixture was <1%, and the $^1$H-NMR spectrum was in accordance with the desired structure.

EXAMPLE E

To 35.7 g (0.052 moles) of the product mixture from example C was added 135 ml of acetone and 1 ml of Dequest 2006 (complexing agent). The mixture was heated to 60° C. and during a period of 30 minutes 8.7 g of 6M KOH solution in water and 9.1 g (0.080 moles) of 30% $H_2O_2$ was added dropwise to the solution. After the addition the reaction mixture was kept at 60° C. for 3 hours. An analysis by $^1$H-NMR revealed that 29% of the nitrile groups had been converted to primary amide groups.

EXAMPLE 1

The foaming behaviour of an epoxidised oleonitrile that had been reacted with a methyl-blocked polyethylene glycol containing 10 (example A) and 14 (example B) polyoxyethylene units respectively, was studied. The foam was measured as mm foam produced in a 500 ml measuring cylinder with 49 mm inner diameter from 200 ml 0.5% surfactant solution when the cylinder was turned around 40 times in one minute. The test was made at room temperature, and the foam height was registered directly and after 1, 5 and 10 minutes. Ethoxylated dihydroxystearonitrile, nonylphenol that had been ethoxylated with 10 moles of ethylene oxide (NF+10 EO) and $C_{12}$–$C_{16}$ alcohol that had been ethoxylated with 7.5 moles of ethylene oxide were used as references. The latter two products are well-known surfactants that are used in cleaning processes.

| Product | Foam height (mm) after 0 min | Foam height (mm) after 1 min | Foam height (mm) after 5 min | Foam height (mm) after 10 min |
| --- | --- | --- | --- | --- |
| Example A | 86 | 51 | 3 | 1–2 |
| Example B | 110 | 85 | 11 | 7 |
| Dihydroxy-stearo-nitrile + 10 EO | 155 | 120 | 7 | 5 |
| Dihydroxy-stearo-nitrile + 14 EO | 172 | 141 | 13 | 10 |
| Example C | 58 | 19 | 8 | 5 |
| Example D | 104 | 100 | 23 | 11 |
| NF + 10EO | >230 | >230 | >230 | >230 |
| $C_{12}$–$C_{16}$ alcohol + 7.5 EO | 220 | 217 | 203 | 176 |

The products according to the present invention produce less foam than the corresponding 9,10-dihydroxystearonitrile derivatives containing the same amount of oxyethylene units. NF+10EO and $C_{12}$–$C_{16}$ alcohol+7.5 EO produce much more foam than any of the products investigated.

EXAMPLE 2

The following recipe was used to prepare formulations containing the surfactants according to the present invention.

| Component | % by weight of component |
| --- | --- |
| Nonionic surfactant | 5 |
| Tetrapotassium pyrophosphate | 6 |
| Sodium metasilicate × 5 $H_2O$ | 4 |
| Hydrotrope (hexyl glucoside) | variable[1] |
| Water | balance |

[1] the amount of hydrotrope added is the minimum amount needed to obtain a clear solution at room temperature The cleaning efficiency of the formulations was evaluated using the following cleaning test: White painted plates were smeared with an oil-soot mixture obtained from diesel engines. 25 ml of the test solutions were poured onto the top of the oil-smeared plates and left there for one minute. The plates were then rinsed off with a rich flow of water. All solutions and the water were kept at a temperature of about 15–20° C. All test solutions were placed on the same plate. The reflectance of the plates was measured with a Minolta Chroma Meter CR-200 reflectometer before and after cleaning.

The test was performed with solutions diluted 1:10 with water. The washed-away soil was calculated by the computer program integrated in the meter, and the results are collected in the table below. One value was obtained for each substance by calculating the mean of four measurements obtained at four different spots on the plate. The values in the table are the mean of the values obtained on two different plates. The reference is a traditional nonionic surfactant obtained by ethoxylation of a C12–C16 alcohol with 7.5 moles of ethylene oxide.

| Surfactant in formulation | % washed away soil with 1:10 dilution |
| --- | --- |
| Example C | 75 |
| Example D | 86 |
| C12–C16 alcohol + 7.5 EO | 76 |

As can be seen from the table, the compounds of the present invention are as good cleaners as the traditional nonionic surfactant used as a reference, and they also have the advantage of being more low-foaming.

What is claimed is:

1. Nonionic compounds of the general formula RY (I), where R is a substituted aliphatic group containing 1–3 structure elements of the formula

(II)

where the carbon atoms shown in the structure element are part of the aliphatic carbon skeleton of group R, which contains 8–24 carbon atoms, and Y is a nitrile group; $R_3$ is an alkyl group with 1–4 carbon atoms; AO is an alkyleneoxy group containing 2–4 carbon atoms and n is a number between 1 and 30.

2. Nonionic compounds of claim 1 containing 1–2 structure elements according to formula (II).

3. Nonionic compounds according to claim 2 where at least 50% of the AO groups are ethyleneoxy groups.

4. Nonionic compounds according to claim 2 where the AO group is the ethyleneoxy group.

5. Nonionic compounds according to claim 1 where at least 50% of the AO groups are ethyleneoxy groups.

6. Nonionic compounds according to claim 1 where the AO group is the ethyleneoxy group.

7. Nonionic compounds according to claim 1 where n is 3–20 and $R_3$ is methyl or ethyl.

8. A surfactant composition which comprises a cleaning effective amount of at least one non-ionic compound of claim 1.

9. The surfactant composition of claim 8 adapted for the cleaning of hard surfaces, vehicle cleaning, bottle cleaning, machine dishwashing or machine washing of textiles.

10. Nonionic compounds of the general formulae

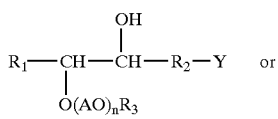
(IIIa)

or

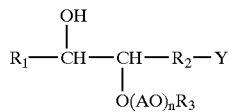
(IIIb)

where $R_1$ is an aliphatic group, $R_2$ is an aliphatic radical, the sum of carbon atoms contained in $R_1$ and $R_2$ is between 9 and 19; Y is a nitrile group; $R_3$ is an alkyl group with 1–4 carbon atoms; AO is an alkyleneoxy group containing 2–4 carbon atoms and n is a number between 1 and 30.

11. Nonionic compounds according to claim 10 where at least 50% of the AO groups are ethyleneoxy groups.

12. Nonionic compounds according to claim 10 where the AO group is the ethyleneoxy group.

13. A method of producing polyoxyalkylene nonionic compounds which comprises a) reacting an epoxidised nitrile containing 1–3 epoxy groups and a total of 8 to 24 carbon atoms with an alkyl blocked polyalkylene glycol having the formula $R_3O(AO)_nH$, where $R_3$ is an alkyl group with 1–4 carbon atoms; AO is an alkyleneoxy group containing 2–4 carbon atoms and n is a number between 1 and 30, in the presence of a catalyst, and optionally subjecting the product obtained to alkaline hydrogen peroxide.

14. A method of producing nonionic compounds of the general formula RY (I), where R is a substituted aliphatic group containing 1–3 structure elements of the formula

(II)

where the carbon atoms shown in the structure element are part of the aliphatic carbon skeleton of group R, which contains 8–24 carbon atoms, and Y is a nitrile or an amide group; $R_3$ is an alkyl group with 1–4 carbon atoms; AO is an alkyleneoxy group containing 2–4 carbon atoms and n is a number between 1 and 30, said method comprising:

reacting an epoxidised nitrile containing 1–3 epoxy groups and a total of 8 to 24 carbon atoms with an alkyl blocked polyalkylene glycol having the formula $R_3O(AO)_nH$, where $R_3$ is an alkyl group with 1–4 carbon atoms; AO is an alkyleneoxy group containing 2–4 carbon atoms and n is a number between 1 and 30, in the presence of a catalyst, and optionally subjecting the product obtained to alkaline hydrogen peroxide.

15. A nonionic compound produced by the method of claim 14.

16. A surfactant composition which comprises a cleaning effective amount of at least one non-ionic compound of claim 15.

17. The surfactant composition of claim 16 adapted for the cleaning of hard surfaces, vehicle cleaning, bottle cleaning, machine dishwashing or machine washing of textiles.

* * * * *